US00PP37710P3

(12) United States Plant Patent
Hansen

(10) Patent No.: US PP37,710 P3
(45) Date of Patent: Sep. 22, 2026

(54) ***IRIS* PLANT NAMED 'Eye Liner'**

(50) Latin Name: ***Iris* x *pseudata (pseudacorus* X *ensata)***
Varietal Denomination: Eye Liner

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,999

(22) Filed: Jan. 14, 2026

(65) Prior Publication Data

US 2026/0262557 P1 Sep. 3, 2026

Related U.S. Application Data

(60) Provisional application No. 63/833,932, filed on Jan. 29, 2025.

(51) Int. Cl.
*A01H 5/02* (2018.01)
*A01H 6/00* (2018.01)

(52) U.S. Cl.
USPC ..... Plt./310
CPC ..... *A01H 6/00* (2018.05)

(58) Field of Classification Search
USPC ..... Plt./310
CPC ..... A01H 5/02
See application file for complete search history.

*Primary Examiner* — Kent L Bell

(57) ABSTRACT

A new and distinct interspecific hybrid *Iris* named 'Eye Liner' with linear, medium-green, foliage topped with lightly branched large flowers on tall scapes. Flowers have very pale lavender to nearly white falls with strong purple veining and bright yellow signal, petaloid stamens, and upright to outwardly standards of white with a butter yellow center. The new plant is useful in the landscape as a specimen, en masse, in a container or as a cut flower.

1 Drawing Sheet

Latin botanical classification: *Iris* x *pseudata* (*pseudacorus* x *ensata*).

Variety denomination: 'Eye Liner'.

STATEMENT REGARDING PRIOR DISCLOSURES UNDER 37 CFR 1.77(B)(6)

The first offer for sale of the claimed plant was with the photograph and brief description on a website operated by Walters Gardens, Inc. first posted on Feb. 1, 2024. Walters Gardens, Inc. obtained *Iris* 'Eye Liner' and all information relating thereto, from the inventor. No plants of *Iris* 'Eye Liner' have been sold in this country or anywhere in the world nor has any disclosure of the new plant been made more than one year prior to the effective filing date of this application and such sale or disclosure within one year was either derived directly or indirectly from the inventor.

BACKGROUND OF THE INVENTION

The present invention, *Iris* 'Eye Liner', relates to a new and distinct cultivar of *Iris*, botanically known as an *Iris* hybrid, more specifically an interspecific *Iris* hybrid between *Iris psedacorus* and *Iris ensata* and given the hybrid status *Iris* x *pseudata*, and is hereinafter referred to by the cultivar name 'Eye Liner' or "the new plant".

'Eye Liner' is the result of a controlled cross by the inventor on Jun. 24, 2013, at a wholesale perennial nursery in Zeeland, Michigan between *Iris pseudacorus* 'Gubijin' (not patented) as the female or seed parent times *Iris ensata* 'Center of Attention' (not patented) as the male or pollen parent. The new plant was first evaluated in the summer of 2015 and the single selected seedling was assigned the breeder code 13-16-1 through the remaining evaluation process until given a cultivar name. 'Eye Liner' was first propagated by division in 2017 by the inventor in Zeeland, Michigan, and subsequently by shoot tip tissue culture. The resultant plants have been true to type in successive generations of asexual propagation.

BRIEF SUMMARY OF THE PLANT

Compared with the new plant, the female parent has a yellow flower with smaller signal pattern and narrower petals, the habit is smaller and slower growing. The male parent has flowers with deep purple veins on light lavender falls that stay more horizontal, the standards are deep purple, the habit is smaller and slower growing.

The closest comparison cultivars known to the inventor are: 'Alabama Blue Fin' (not patented), 'Byakuya No Kumi' (not patented), 'Cat's Eye' (not patented), 'Kinshikou' (not patented), 'Okagami' (not patented), 'Shirabyoshi' (not patented), 'Shirogai' (not patented), 'Shoryu No Mai' (not patented), 'Takamagahara' (not patented), 'Take No Sato' (not patented), and 'Yukiyanagi' (not patented).

'Alabama Blue Fin' has flowers with more cream-colored falls that have purple veins that extend less than 10 mm from the outside of the signal, and the standards are more yellowish. 'Byakuya No Kumi' has cream-colored to lightly lavender falls that have purple veins that extend less than 20 mm from the outer signal. 'Cat's Eye' is a cleaner creamy-white in the distal fall petals and the purple veining does not extend to the margin. 'Kinshikou' has flowers that are yellowish with a rose overlay and the purple veins extend less than half-way to the petal margin. 'Okagami' has more purple blush in the signal and less distinct purple veining in the fall. 'Shirabyoshi' has more pronounce purple veining in the signal and the purple veining in the fall extends only about 5 mm from the purple rim around the signal. 'Shirogai' has a softer yellow signal, and light blush of yellow in the fall, and the purple veins do not extend as far toward the margin. 'Shoryu No Mai', 'Takamagahara', and 'Take No Sato' all have purplish standards and a stronger purplish blush in the fall. 'Yukiyanagi' has a more whitish fall with less purple veining, and the standard has a faint purplish blush.

The following traits have been repeatedly observed and represent the unique characteristics of the new cultivar. These attributes in combination distinguish 'Eye Liner' as a new and unique cultivar of *Iris:*

1. Foliage is medium green with a variable height of three feet and growing to four feet tall with an abundance of water;
2. Flower stems are lightly-branched with large flowers;
3. Flower falls are very pale lavender to near white with strong purple veining reaching nearly to the margins;
4. Flower signal is bright yellow;
5. Flower standards are white with a butter yellow center;

BRIEF DESCRIPTION OF THE DRAWING

The accompanying colored photograph illustrates the overall appearance of a three-year-old plant of *Iris* 'Eye Liner', including the unique traits. The plant used in the photograph was grown in full-sun trial gardens in Zeeland, Michigan. The colors are as accurate as reasonably possible with color reproductions. Ambient light spectrum, temperature, source, and direction may cause the appearance of minor variations in color.

The drawing shows the new cultivar with flowers and buds.

DETAILED BOTANICAL DESCRIPTION OF THE PLANT

The following descriptions and color references are based on the 2015 edition of The Royal Horticultural Society Colour Chart except where common dictionary terms are used. The new plant, *Iris* 'Eye Liner', has not been observed in all possible environments. The phenotype may vary slightly with different environmental conditions, such as temperature, light, fertility, moisture, and maturity levels, but without any change in the genotype. The following observations and size descriptions are of a three-year-old plant in a full-sun display garden in Zeeland, Michigan with supplemental water and fertilizer.

Parentage: The female (seed) parent is 'Gibijin', the male (pollen) parent is 'Center of Attention';

Plant habit: Winter-hardy, clumping; upright vase-shaped; herbaceous perennial;

Size: Foliage height to about 114 cm tall and about 76 cm wide in a 3.8-liter container grown in a greenhouse; about four to seven divisions of fans; flowering to about 96 cm tall;

Root: Fleshy; wiry; color nearest RHS NN155A;

Rhizome size: To about 1 cm wide and up to about 6 cm long; color nearest RHS 177B;

Propagation: Rhizome division in early spring, late summer, or fall;

Growth rate: Vigorous; increasing from 3 to 7 rhizomes per original single rhizome in a single growing season;

Leaf: Linear; simple; conduplicate; equitant; alternate; sheathed to base of rhizome; apex acute; margin entire; both surfaces glabrous and slightly glaucous; comprising a fan with new growth in center; aspect upright, arching distally;

Leaf size: Variable, increasing with ample water to about 124 cm long and 3 cm wide;

Leaf quantity: To about 7 to 9 per fan;

Leaf color: Emerging between RHS 146A and RHS 137B; mature slightly more grey than RHS NN137A;

Leaf venation: Parallel; not prominent; color slightly more grey than RHS NN137A;

Pedicel: Cylindrical; glabrous; slightly lustrous; to about 11 cm long and 4 mm diameter, average about 3.7 cm long;

Pedicel color: Nearest RHS 145C;

Peduncle: Scape; round; slightly ovoid; pithy; one per mature fan under normal growing conditions; aspect upright; size to about 116 cm in length and 10 cm diameter at base; surfaces glabrous, slightly lustrous;

Peduncle color: Between RHS 144A and RHS 144B;

Cauline leaves or scape bracts: Simple; linear; conduplicate; about one per flower below flower; to about 30 cm long and up to 2.5 cm across, clasping base; acute apex; aspect mostly upright; color slightly more grey than RHS NN137A;

Flower description: Single; perianth tubular comprised two pairs of three petals; three outer petals form broad drooping falls narrowing toward base, three inner petals form upright standards, petaloid style arms branch over the falls;

Flower size: To about 9 cm across and 6 cm tall;

Blooming period: About 2 to 3 weeks starting early to mid-June;

Lastingness of inflorescence: About 2 weeks from first opening bloom to fading of last opening bloom, individual flowers last about 2 days;

Flower fragrance: None detected;

Flower number: 5 to 7 per scape;

Flower bud: Shape oblong terete; apex narrowly acute; base truncate; size to about 6 cm long and to about 1.2 cm diameter near middle;

Flower bud color: Distally nearest RHS 4D; proximally between RHS 151D and RHS 145B with veins in the middle of nearest RHS 79A and a shadow ring about 1 to 2 mm wide of a light blush of nearest RHS 79A;

Falls: Three; broadly spatulate; rounded apex; attenuate base; entire margin; mostly flat; arching downward distally; glabrous adaxial and abaxial; about 5 cm wide and 8 cm long;

Falls color: Adaxial signal nearest RHS 6B with few narrow veins of nearest RHS 79A, signal surrounded by an eye shadow of between RHS 79B and RHS 79C; portion distal to eye shadow nearest RHS NN155C with faint blush of nearest RHS 79B concentrated toward signal to nearest RHS NN155C at margin, with veins of nearest RHS 79A extending to the margin; fall base between RHS 10B and RHS 11B both adaxial and abaxial; adaxial distal portion nearest RHS NN155C with a faint blush of nearest RHS 79B and veins nearest RHS 79A extending to the margin;

Standards: Three; spatulate; stipitate; rounded apex; attenuate base; entire margin; glabrous adaxial and abaxial;

Standard size: Blade to about 2.5 cm long and 1.2 cm wide near apex; stalk to about 1 cm long and 1.5 mm across;

Standards color: Adaxial and abaxial distal blade two-thirds nearest RHS NN155D, adaxial and abaxial stalk one-third between RHS 8B and RHS 8C; with veining indistinguishable;

Gynoecium: Three; showy; petaloid; reflexed about 100 degrees distally; to about 5.5 cm long and 1.7 cm across near apex;

*Style*.—Petaloid, stipitate; margin irregularly crenate; divided into distal crest and proximal arm; style crest apices acute, free in the distal 1.3 cm, individually 1.1 cm wide in distal free portion, reflexed in distal 1 cm; arm fused and stipitate, margin irregularly crenate, blade to about 4.2 cm long and 1.1 cm across at crest, stalk 1.2 cm long, 3 mm wide at blade, and 1.5 mm wide at base; blade base truncate; color in adaxial and abaxial proximal fused center between RHS 12B and RHS 12C lightening to nearest RHS 11D in crest and in arm toward margins.

*Style flap or spur*.—At separation of style lobes just below the stigma; hyaline; to about 1 cm wide and 1.5 mm long; color nearest RHS 11D.

*Stigma*.—About 3 mm long, 5 mm across, deltoid, color NN155B.

*Ovary*.—Inferior; about 2.4 cm tall and about 6 mm across; color nearest RHS 144B.

Androecium: Three; adnate to base of falls; about 3.4 cm long;

*Filament*.—Applanate; about 2 cm long, 3 mm wide near middle, and 1 mm thick; adnate with adaxial fall in basal 1 cm; color distally nearest RHS 1D and proximally nearest RHS N144A.

*Anthers*.—Basifixed; longitudinal; about 14 mm long and 2 mm across, color adaxial between RHS 10C and RHS 10D, abaxial nearest 79D.

*Pollen*.—Moderate production; color nearest RHS 12A.

Fruit and seed: Not observed;

Hardiness: From USDA hardiness zone 4 to 9;

Growth: Prefers full sun to light shade; moist soils of moderate fertility;

Diseases and pests: No susceptibility or resistance to diseases or pests except that which is common to *Iris*.

I claim:

1. A new and distinct cultivar of *Iris* plant named 'Eye Liner' as herein illustrated and described.

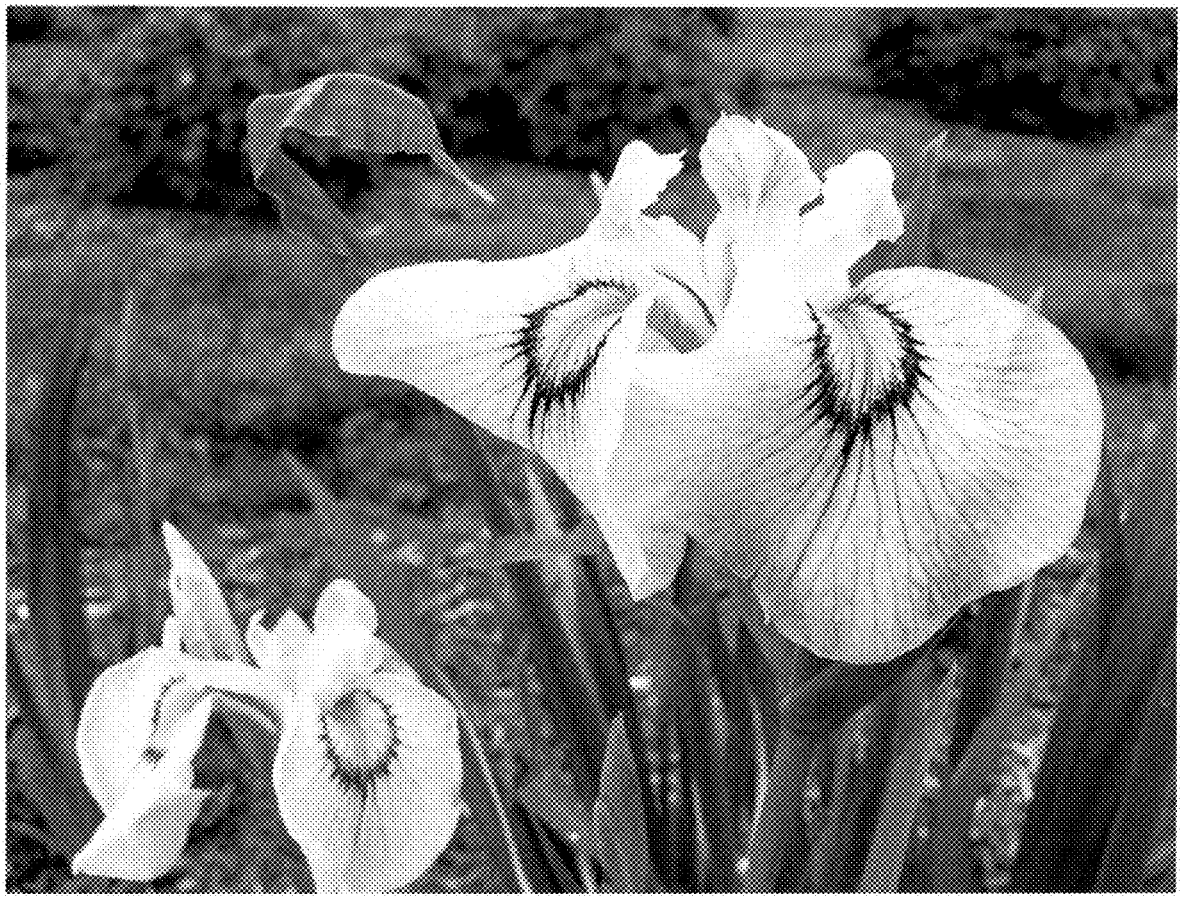

* * * * *